(12) United States Patent
Cerundolo

(10) Patent No.: US 7,833,244 B2
(45) Date of Patent: Nov. 16, 2010

(54) SUTURE FIXATION DEVICE AND METHOD FOR SURGICAL REPAIR

(75) Inventor: Daniel Cerundolo, Hingham, MA (US)

(73) Assignee: Arthroscopic Innovations LLC, Weymouth, MA (US)

( * ) Notice: Subject to any disclaimer, the term of this patent is extended or adjusted under 35 U.S.C. 154(b) by 836 days.

(21) Appl. No.: 11/110,419

(22) Filed: Apr. 20, 2005

(65) Prior Publication Data

US 2006/0241694 A1 Oct. 26, 2006

(51) Int. Cl.
*A61B 17/04* (2006.01)
*A61F 5/00* (2006.01)

(52) U.S. Cl. ..................................................... 606/232

(58) Field of Classification Search .................. 606/300, 606/232, 224, 233, 86, 87, 96, 98, 86 R; 623/11.11, 623/13.11–13.19
See application file for complete search history.

(56) References Cited

U.S. PATENT DOCUMENTS

| | | | |
|---|---|---|---|
| 3,976,079 | A | 8/1976 | Samuels et al. |
| 4,103,683 | A | 8/1978 | Neufeld |
| 4,535,768 | A | 8/1985 | Hourahane et al. |
| 4,633,869 | A | 1/1987 | Schmieding |
| 4,672,957 | A | 6/1987 | Hourahane |
| 4,722,331 | A | 2/1988 | Fox |
| 4,739,751 | A | 4/1988 | Sapega et al. |
| 4,781,182 | A | 11/1988 | Purnell et al. |
| 4,920,958 | A | 5/1990 | Walt et al. |
| 4,945,904 | A | 8/1990 | Bolton et al. |
| 5,042,983 | A | 8/1991 | Rayhack |
| 5,112,337 | A | 5/1992 | Paulos et al. |
| 5,163,940 | A | 11/1992 | Bourque |
| 5,178,621 | A | 1/1993 | Cook et al. |

(Continued)

FOREIGN PATENT DOCUMENTS

EP 0755656 A2 1/1997

(Continued)

OTHER PUBLICATIONS

Notice of Allowance in U.S. Appl. No. 11/110,004, dated Feb. 21, 2007.

(Continued)

*Primary Examiner*—(Jackie) Tan-Uyen T Ho
*Assistant Examiner*—Dianne Dornbusch
(74) *Attorney, Agent, or Firm*—Wolf, Greenfield & Sacks, P.C.

(57) ABSTRACT

An apparatus and method for suture fixation. A suture fixation device includes a body having an inner end and an outer end and a pathway. A restriction may be provided in the pathway that relatively freely permits movement of a suture through the pathway in a first direction and inhibits movement of the suture through the pathway in a second direction. A suture provided in a passageway formed in bone may be secured at an opening into the passageway using a suture fixation device that has a portion positioned outside of and adjacent the opening in contact with portions of cortical bone. The suture fixation device may include a flange portion adapted to be positioned outside of and adjacent a suitably sized hole formed in tissue, such as bone. An inner end of the suture fixation device may extend from the flange portion and be positioned in the hole adjacent cancellous bone.

20 Claims, 6 Drawing Sheets

U.S. PATENT DOCUMENTS

| | | | |
|---|---|---|---|
| 5,211,647 | A | 5/1993 | Schmieding |
| 5,217,471 | A | 6/1993 | Burkhart |
| 5,222,962 | A | 6/1993 | Burkhart |
| 5,234,434 | A | 8/1993 | Goble et al. |
| 5,269,786 | A | 12/1993 | Morgan |
| 5,320,626 | A | 6/1994 | Schmieding |
| 5,330,468 | A | 7/1994 | Burkhart |
| 5,334,205 | A | 8/1994 | Cain |
| 5,350,383 | A | 9/1994 | Schmieding et al. |
| 5,368,596 | A | 11/1994 | Burkhart |
| 5,403,321 | A | 4/1995 | DiMarco |
| 5,425,733 | A | 6/1995 | Schmieding |
| 5,431,651 | A | 7/1995 | Goble |
| 5,466,243 | A | 11/1995 | Schmieding et al. |
| 5,575,801 | A | 11/1996 | Habermeyer et al. |
| 5,601,562 | A | 2/1997 | Wolf et al. |
| 5,603,716 | A | 2/1997 | Morgan et al. |
| 5,620,449 | A | 4/1997 | Faccioli et al. |
| 5,626,613 | A | 5/1997 | Schmieding |
| 5,681,333 | A | 10/1997 | Burkhart et al. |
| 5,683,401 | A | 11/1997 | Schmieding et al. |
| 5,690,677 | A | 11/1997 | Schmieding et al. |
| 5,743,916 | A | 4/1998 | Greenberg et al. |
| 5,746,752 | A | 5/1998 | Burkhart |
| 5,766,179 | A | 6/1998 | Faccioli et al. |
| 5,833,691 | A | 11/1998 | Bimman |
| RE36,020 | E | 12/1998 | Moore et al. |
| 5,860,978 | A * | 1/1999 | McDevitt et al. ............ 606/232 |
| 5,918,604 | A | 7/1999 | Whelan |
| 5,919,196 | A | 7/1999 | Bobic et al. |
| 5,931,869 | A * | 8/1999 | Boucher et al. ............ 128/898 |
| 5,951,559 | A | 9/1999 | Burkhart |
| 5,964,783 | A | 10/1999 | Grafton et al. |
| 5,993,451 | A | 11/1999 | Burkhart |
| 6,013,083 | A * | 1/2000 | Bennett ...................... 606/104 |
| 6,027,523 | A | 2/2000 | Schmieding |
| 6,039,742 | A | 3/2000 | Krettek et al. |
| 6,074,403 | A | 6/2000 | Nord |
| 6,110,207 | A * | 8/2000 | Eichhorn et al. ......... 623/13.14 |
| 6,113,604 | A | 9/2000 | Whittaker et al. |
| 6,117,162 | A | 9/2000 | Schmieding et al. |
| 6,120,511 | A | 9/2000 | Chan |
| 6,132,433 | A | 10/2000 | Whelan |
| 6,214,031 | B1 | 4/2001 | Schmieding et al. |
| 6,267,766 | B1 | 7/2001 | Burkhart |
| 6,270,503 | B1 | 8/2001 | Schmieding |
| 6,319,270 | B1 | 11/2001 | Grafton et al. |
| 6,371,124 | B1 | 4/2002 | Whelan |
| 6,387,129 | B2 | 5/2002 | Rieser et al. |
| 6,416,518 | B1 | 7/2002 | DeMayo |
| 6,461,373 | B2 * | 10/2002 | Wyman et al. ............ 606/232 |
| 6,491,714 | B1 * | 12/2002 | Bennett ...................... 606/232 |
| 6,511,499 | B2 | 1/2003 | Schmieding et al. |
| 6,517,552 | B1 | 2/2003 | Nord et al. |
| 6,517,564 | B1 | 2/2003 | Grafton et al. |
| 6,524,317 | B1 * | 2/2003 | Ritchart et al. ............ 606/232 |
| 6,537,319 | B2 | 3/2003 | Whelan |
| 6,540,750 | B2 | 4/2003 | Burkhart |
| 6,544,281 | B2 | 4/2003 | ElAttrache et al. |
| 6,575,976 | B2 | 6/2003 | Grafton |
| 6,592,588 | B1 | 7/2003 | Bobic et al. |
| 6,616,665 | B2 | 9/2003 | Grafton et al. |
| 6,616,674 | B2 | 9/2003 | Schmieding |
| 6,623,524 | B2 | 9/2003 | Schmieding |
| 6,629,977 | B1 | 10/2003 | Wolf |
| 6,641,597 | B2 | 11/2003 | Burkhart et al. |
| 6,652,563 | B2 | 11/2003 | Dreyfuss |
| 6,656,183 | B2 * | 12/2003 | Colleran et al. ............ 606/232 |
| 6,663,656 | B2 | 12/2003 | Schmieding et al. |
| 6,716,234 | B2 | 4/2004 | Grafton et al. |
| 6,733,529 | B2 | 5/2004 | Whelan |
| 6,878,166 | B2 * | 4/2005 | Clark et al. ............... 623/13.12 |
| 6,886,569 | B2 * | 5/2005 | Chervitz et al. ............. 128/898 |
| 6,994,725 | B1 * | 2/2006 | Goble ...................... 623/13.14 |
| 7,032,599 | B2 | 4/2006 | May et al. |
| 7,527,648 | B2 * | 5/2009 | May et al. ................ 623/13.12 |
| 7,530,999 | B2 * | 5/2009 | Clark et al. ............... 623/13.12 |
| 7,569,059 | B2 * | 8/2009 | Cerundolo ................ 606/86 R |
| 2001/0008971 | A1 * | 7/2001 | Schwartz et al. ............ 606/232 |
| 2001/0037119 | A1 | 11/2001 | Schmieding |
| 2001/0037131 | A1 | 11/2001 | Schmieding et al. |
| 2001/0051807 | A1 | 12/2001 | Grafton |
| 2002/0013608 | A1 | 1/2002 | ElAttrache et al. |
| 2002/0022862 | A1 | 2/2002 | Grafton et al. |
| 2002/0032466 | A1 | 3/2002 | Grafton et al. |
| 2002/0065528 | A1 * | 5/2002 | Clark et al. .................. 606/151 |
| 2002/0120275 | A1 | 8/2002 | Schmieding et al. |
| 2002/0143364 | A1 | 10/2002 | Burkhart |
| 2003/0004545 | A1 | 1/2003 | Burkhart et al. |
| 2003/0050666 | A1 | 3/2003 | Grafton |
| 2004/0093031 | A1 | 5/2004 | Burkhart et al. |
| 2004/0106950 | A1 | 6/2004 | Grafton et al. |
| 2004/0133239 | A1 * | 7/2004 | Singhatat ..................... 606/232 |
| 2004/0172062 | A1 | 9/2004 | Burkhart |
| 2004/0204724 | A1 | 10/2004 | Kissel et al. |
| 2005/0038437 | A1 | 2/2005 | McDevitt et al. |
| 2005/0197662 | A1 * | 9/2005 | Clark et al. .................... 606/98 |
| 2006/0241619 | A1 * | 10/2006 | Cerundolo .................... 606/72 |
| 2006/0241620 | A1 * | 10/2006 | Cerundolo .................... 606/72 |
| 2006/0241657 | A1 * | 10/2006 | Cerundolo .................. 606/148 |
| 2006/0241658 | A1 * | 10/2006 | Cerundolo .................. 606/148 |
| 2007/0005067 | A1 * | 1/2007 | Dross .......................... 606/72 |
| 2007/0208356 | A1 * | 9/2007 | Cerundolo .................. 606/148 |

FOREIGN PATENT DOCUMENTS

| | | |
|---|---|---|
| EP | 0 824 893 A1 | 2/1998 |
| EP | 1013229 A2 | 6/2000 |
| WO | WO 01/97677 A2 | 12/2001 |

OTHER PUBLICATIONS

Office Action in U.S. Appl. No. 11/110,540, dated Oct. 9, 2007.

International Search Report and Written Opinion for International Application No. PCT/US2006/013929 dated Mar. 21, 2007.

Arthrex, Shoulder Arthroscopy & Mini-Open Repairs, TissueButton™, printed from www.arthrex.com, 2005.

ArthroCare Corporation, Atlantech® Collection, ACL Reconstruction Instrumentation, Bilok® ACL Reconstruction Interference Screws, Suture Anchors, Handheld Instruments, Shoulder Retractor, CAPS-LOCK™ Shoulder Cannual, Chondra Pick Instruments, www.arthrocare.com/sports_medicine/sm_phy_products_atlantech.htm, Jan. 5, 2005, © 2004 ArthroCare Corporation.

Bio-Phase™ II Suture Anchor, © 2003 Arthrotek, Inc., www.arthrotek.com/products/anchors_biophaseii.cfm.

Brochure: Closing the Gap in Soft Tissue Repair, The AutoCuff System, Opus Medical, Inc., 2004, A1006-0504.

Burkhart et al., Arthroscopic Rotator Cuff Repair: Analysis of Results by Tear Size and by repair Technique—Margin Convergence Versus Direct Tendon-To-Bone Repair, 2001, Journal of Arthroscopic and Related Surgery, vol. 17, No. 9 (Nov.-Dec. 2001), pp. 905-912.

Burkhart et al., Arthroscopic Subscapularis Tendon Repair: Technique and Preliminary Results, 2002, Journal of Arthroscopic and Related Surgery, vol. 18, No. 5 (May-Jun.), pp. 454-463.

Burkhart et al., Clinical and Anatomic Considerations in the Use of a New Anterior Inferior Subaxillary Nerve Arthroscopy Portal, 1996, Journal of Arthroscopic and Related Surgery, vol. 12, No. 5 (Oct.), pp. 634-637.

Burkhart et al., Shoulder Arthroscopy New Concepts, 1996, Arthroscopic Surgery, Part 1 (Clinics in Sports Medicine) vol. 15, No. 4 (Oct.), pp. 635-653.

Burkhart et al., Slap Lesions in the Overhead Athlete, 2001, Orthopedic Clinics of North America, Vo. 32, No. 3 (Jul. 2001).

Burkhart, A Stepwise Approach to Arthroscopic Rotator Cuff Repair Based on Biomechanical Principles, 2000, Journal of Arthroscopic and Related Surgery, vol. 16, No. 1, pp. 82-90.

Burkhart, Arthroscopic Treatment of Massive Rotator Cuff Tears, Sep. 2001, Clinical Orthopaedics and Related Research vol. 1 (390), pp. 107-118.

Burkhart, Biomechanics of Rotator Cuff Repair: Converting the Ritual to a Science, AAOS Instructional Course Lectures, vol. 47, pp. 43-50, 1998.

Burkhart, Partial Repair of Massive Rotator Cuff Tears: The evolution of a Concept, 1997, The Rotator Cuff, Part 1 (Orthopedic Clinics of North America), vol. 28, No. 1, pp. 125-132.

Burkhart, Shoulder Scope: Corkscrew Rotator Cuff Repair, Arthroscopic Knot Tying, www.shoulder.com, San Diego Shoulder Arthroscopy Inc., 1997.

Burkhart, Shoulder Scope: Corkscrew Rotator Cuff Repair, Corkscrew Insertion, www.shoulder.com, San Diego Shoulder Arthroscopy Inc., 1997.

Burkhart, Shoulder Scope: Corkscrew Rotator Cuff Repair, Corkscrew Insertion, www.shoulder.com, San Diego Shoulder Arthroscopy Inc., 1997.

Burkhart, Shoulder Scope: Corkscrew Rotator Cuff Repair, Dual Corkscrew and Matress Suture Technique (1 of 2), www.shoulder.com, San Diego Shoulder Arthroscopy Inc., 1997.

Burkhart, Shoulder Scope: Corkscrew Rotator Cuff Repair, Dual Corkscrew and Matress Suture Technique (2 of 2), www.shoulder.com, San Diego Shoulder Arthroscopy Inc., 1997.

Burkhart, Shoulder Scope: Corkscrew Rotator Cuff Repair, Knot Completion, www.shoulder.com, San Diego Shoulder Arthroscopy Inc., 1997.

Burkhart, Shoulder Scope: Corkscrew Rotator Cuff Repair, Mini-Open Incision, www.shoulder.com, San Diego Shoulder Arthroscopy Inc., 1997.

Burkhart, Shoulder Scope: Corkscrew Rotator Cuff Repair, Patient Positioning, www.shoulder.com, San Diego Shoulder Arthroscopy Inc., 1997.

Burkhart, Shoulder Scope: Corkscrew Rotator Cuff Repair, Portal Placement, www.shoulder.com, San Diego Shoulder Arthroscopy Inc., 1997.

Burkhart, Shoulder Scope: Corkscrew Rotator Cuff Repair, Rotator Cuff Mobilization, www.shoulder.com, San Diego Shoulder Arthroscopy Inc., 1997.

Burkhart, Shoulder Scope: Corkscrew Rotator Cuff Repair, Suture Placement and Knot Tying, www.shoulder.com, San Diego Shoulder Arthroscopy Inc., 1997.

Burkhart, Shoulder Scope: Corkscrew Rotator Cuff Repair, Suture Retrieval, www.shoulder.com, San Diego Shoulder Arthroscopy Inc., 1997.

Burkhart, Shoulder Scope: Corkscrew Rotator Cuff Repair, Trough Preparation, www.shoulder.com, San Diego Shoulder Arthroscopy Inc., 1997.

Burkhart, Shoulder Scope: Corkscrew Rotator Cuff Repair, Vertical Switch Preparation, www.shoulder.com, San Diego Shoulder Arthroscopy Inc., 1997.

Burkhart, Tissue Fixation Security in Transosseous Rotator Cuff Repairs: A Mechanical Comparison of Simple Versus Mattress Sutures, 1996, Journal of Arthroscopic and Related Surgery, vol. 12, No. 6 (Dec.), pp. 704-708.

Cole et al., Anthroscopic Treatment of Anterior Glenohumeral Instability: Indications and Techniques, AAOS Instructional Course Lectures, vol. 53, pp. 545-558 (2004).

CurvTek website information re: Arthrotek CurvTek Bone Tunneling System, Jan. 7, 2005.

Gartsman, Arthroscopic Rotator Cuff Repair, Area Spalla, Arthroscopic, vol. III, N1, 2002, pp. 18-25.

Hawkins et al., The AutoCuff System for Rotator Cuff Repair (Surgical Technique), Opus Medical, Inc., 2004, A1022-06/04.

Higgins et al., Acromioclavicular Separation, Anatomical Chart Co., 1988.

http://home.flash.net/~rustyj/RCR.gif Anatomy of the Rotator Cuff, Rotator Cuff Repair, Jan. 5, 2005.

Johnson &Johnson, DePuy Mitek, Inc., Launches SPIRALOK™, the Latest Innovation in Minimally Invasive Rotator Cuff Repair, www.jnj.com/news/jnj_news/20040310_110538.htm, 2004.

Kessler, et al., Arthrotek, Inc., RCB™ Rotator Cuff Buttress © 2003 Arthrotek, Inc.

Linvatec Corporation, Mini-Open Rotator Cuff Repair System, Shutt® Suture Punch System, Tissue Repair Systems, Spectrum® Tissue Repair System www.Linvatec.com 2004.

Lo et al., Arthroscopic Coracoplasty Through the Rotator Interval, 2003, Journal of Arthroscopic and Related Surgery, vol. 19, No. 6 (Jul.-Aug.), pp. 667-671.

Lo et al., Arthroscopic Repair of Massive, Contracted, Immobile Rotator Cuff Tears Using Single and Double Interval Slides: Technique and Preliminary Results, 2004, Journal of Arthroscopic and Related Surgery, vol. 20, No. 1 (Jan.), pp. 22-33.

Lo et al., Combined Subcoracoid and Subacromial Impingement in Association with Anterosuperior Rotator Cuff Tears: An Arthroscopic Approach, 2003, Journal of Arthroscopic and Related Surgery, vol. 19, No. 10 (Dec.), pp. 1068-1078.

Lo et al., Current Concepts in Arthroscopic Rotator Cuff Repair, 2003, American Journal of Sports Medicine, vol. 31, No. 2, pp. 308-324.

Lo et al., Double-Row Arthroscopic Rotator Cuff Repair: Re-Establishing the Footprint of the Rotator Cuff, 2003, Journal of Arthroscopic and Related Surgery, Vo. 19, No. 9 (Nov.), pp. 1035-1042.

Lo et al., The Interval Slide in Continuity: A Method of Mobilizing the Anterosuperior Rotator Cuff Without Disrupting the Tear Margins, 2004, Journal of Arthroscopic and Related Surgery, vol. 20, No. 4 (Apr.) pp. 435-441.

Lo et al., Triple Labral Lesions: Pathology and Surgical Repair Technique—Report of Seven Cases, 2005, Journal of Arthroscopic and Related Surgery, vol. 21, No. 2 (Feb.) pp. 186-193.

Opus Medical: Technology, www.opusmedical.com/technology.htm, Advanced Technology For Totally Arthroscopic Rotator Cuff Repair, Jan. 5, 2005, pp. 1-3.

Richards et al., Arthroscopic Humeral Avulsion of the Glenohumeral Ligaments (HAGL) Repair, Journal of Arthroscopic and Related Surgery, 2004, vol. 20, No. 6, pp. 134-141.

Richards et al., Arthroscopic-Assisted Biceps Tenodesis for Rupture of the Long Head of Biceps Brachii: The Cobra Procedure, 2004, Journal of Arthroscopic and Related Surgery, vol. 20, No. 6 (Jul.-Aug.), pp. 201-207.

Richards et al., Margin Convergence of the Posterior Rotator Cuff to the Biceps Tendon, 2004, Journal of Arthroscopic and Related Surgery, vol. 20, No. 7 (Sept.), pp. 771-775.

Richards et al., Subscapularis Tears: Arthroscopic Repair Techniques, 2003, Orthop. Clin. N. Am. vol. 34, pp. 485-498.

Rotator Cuff Repair, www.shands.org/health/information/article/007207.htm, 2003.

Ryu et al., Complex Topics in Arthroscopic Subacromial Space and Rotator Cuff Surgery, 2002, Journal of Arthroscopic and Related Surgery, vol. 18, No. 2 (Feb., Suppl. 1), pp. 51-64.

Shoulder Solutions—Shoulder Anatomy—Shoulder Bones, www.shouldersolutions.com/anatomy_2.php Jan. 5, 2005.

Shoulder Solutions—Shoulder Anatomy—Shoulder Muscles and Tendons, www.shouldersolutions.com, Jan. 5, 2005.

Smith&Nephew, RotorloC Absorbable Rotator Cuff Suture Anchor, Smith and Nephew Endoscopy, http://endo.smith-nephew.com, Jan. 5, 2005.

Smith&Newphew, Cannula Line, Aug. 17, 2004 www.smith-newphew.com.

Surgical Solutions, Inc. ExpressSew Suture Passer, Suture Passing System, The 5mm solution for tissue repair, © 2004 Surgical Solutions, Inc.

University of Washington Orthopaedics & Sports Medicine, Surgery for Rotator Cuff Tears, Rotator cuff tears of the shoulder, www.orthop.washington.edu/faculty/Matsen/rotatorcuffsurgery/05, Edited by Frederick A. Matsen III, M.D., pp. 1-4, 2003.

University of Washington Orthopaedics & Sports Medicine, Surgery for Rotator Cuff Tears, About rotator cuff surgery, www.orthop.washington.edu/faculty/Matsen/rotatorcuffsurgery/05, Edited by Frederick A. Matsen III, M.D., pp. 1-2, 2003.

University of Washington Orthopaedics & Sports Medicine, Surgery for Rotator Cuff Tears, About surgery for rotator cuff tears, www.orthop.washington.edu/faculty/Matsen/rotatorcuffsurgery/05, Edited by Frederick A. Matsen III, M.D., pp. 1-2, 2003.

Uribe, Closing the Gap in Arthroscopic Rotator Cuff Repair: A Review of Our Experience with 40 Cases Using the AutoCuff System, Opus Medical, Inc., 2004, A1021-03/04.

Worland, et al., Arthrotek, Rotator Cuff Repair, RC Needle, www.arthrotek.com ©2000, Arthrotek, Inc.

* cited by examiner

SUTURE FIXATION DEVICE AND METHOD FOR SURGICAL REPAIR

BACKGROUND OF INVENTION

1. Field of Invention

This invention relates to a suture fixation device and method for surgical repair.

2. Discussion of Related Art

Suture anchors and other suture fixation devices are often used for surgical repair, such as when attempting to secure one body portion relative to another or relative to a surgical implant or other device. For example, tendon damage frequently requires surgery for repair, e.g., to reattach a torn or separated tendon to the bone to which the tendon would normally be attached. Shoulder rotator cuff injuries typically involve damage to the rotator cuff tendon such that the tendon, or at least a portion thereof, requires reattachment to the humerus. FIG. 1 shows a schematic diagram of a humerus 1 and a portion of a rotator cuff tendon 2 that is normally attached to the head of the humerus. In one type of damage to the rotator cuff, the tendon 2 may detach or be partially torn from the humerus 1, such as that shown schematically in FIG. 2. Such damage may be repaired by reattaching the rotator cuff tendon to the humerus 1 by a suture or other fixation so that the body's normal healing processes can naturally effect reattachment of the tendon to the bone. One repair technique for reattaching the rotator cuff 2 to the humerus 1 involves fixing an anchor 101 at a margin between the articulating portion 11 of the humerus 1 and the humerus' greater tuberosity 12. A suture 102 is secured to the rotator cuff 2 and the anchor 101, and the suture 102 is tensioned so that the rotator cuff 2 is held in place close to the humerus 1. Thereafter, the body may reestablish the proper attachment of the rotator cuff 2 to the humerus 1.

SUMMARY OF INVENTION

In one aspect of the invention, a rotator cuff repair technique is provided that does not necessarily require placement of an anchor at a margin between the articulating surface and the greater tuberosity of the humerus. In one embodiment, a suture fixation device, if provided, may be positioned at a lateral side of the humerus, away from the rotator cuff/humerus attachment point.

Other aspects of the invention are provided that are not necessarily restricted to use in rotator cuff repair. For example, in one aspect of the invention, a passageway may be formed through a body portion by forming first and second intersecting holes in the body portion. A tissue, prosthetic or other material may be secured relative to the body portion using a suture that passes through the passageway. In one aspect of the invention, a suture may be passed through the passageway and secured using a suture fixation device arranged to engage with the body portion near an opening of the passageway.

In one aspect of the invention, a suture fixation device includes a body having an inner end and an outer end and a pathway extending between the inner and outer ends. The inner end may be arranged to be positioned in a hole, such as in bone, and the body may include a restriction in the pathway that relatively freely permits movement of a knotless suture through the pathway in a first direction and inhibits movement of the knotless suture through the pathway in a second direction opposite the first direction.

In another aspect of the invention, a method includes forming a passageway in bone, where the passageway extends from an opening into the bone. A suture may be provided in the passageway so that the suture extends from within the bone toward the opening. The suture may be secured relative to the bone at the opening using a suture fixation device that has a portion positioned outside of and adjacent the opening in contact with portions of cortical bone.

In another aspect of the invention, a suture fixation device may include an outer end including a flange portion adapted to be positioned outside of and adjacent a suitably sized hole formed in bone that extends from a cortical surface into cancellous bone. The flange portion may be positionable so as to contact cortical bone around the hole. An inner end may extend from the flange portion and be adapted to be positioned in the hole adjacent cancellous bone. The device may be arranged to secure, relative to the bone, a suture extending from within the hole toward the flange portion.

In another aspect of the invention, a method includes forming a passageway through a body portion, where the passageway extends from a first opening near a material to be secured relative to the body portion to a second opening positioned away from the material. A suture may be secured to the material, where the suture has two ends extending from the material. The two ends of the suture may be positioned in the passageway, and the two ends of the suture may be secured relative to the body portion near the second opening.

BRIEF DESCRIPTION OF DRAWINGS

Various aspects of the invention are described with reference to illustrative embodiments, wherein like numerals reference like elements, and wherein.

DETAILED DESCRIPTION

Figure 1:
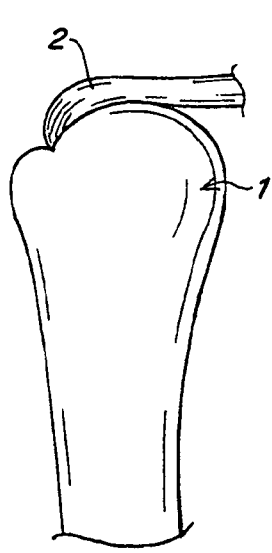
FIG. 1 is a schematic diagram of a head of a humerus and attached rotator cuff tendon.
Figure 2:
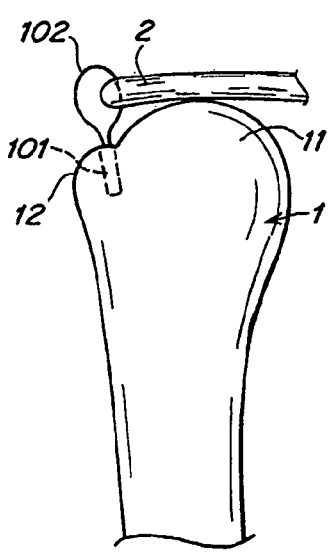
FIG. 2 shows a prior art technique for repairing a rotator cuff injury.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting.

Various aspects of the invention are described below with reference to specific embodiments. For example, aspects of the invention are described in the context of performing a rotator cuff repair. However, it should be understood that aspects of the invention are not necessarily restricted to rotator cuff repair techniques, or even to surgical techniques performed on a shoulder. Rather, various aspects of the invention may be used in any suitable surgical procedure. In addition, various aspects of the invention may be used alone, and/or in combination with any other aspects of the invention.

In one aspect of the invention, a method for performing a surgical procedure may include providing a passageway in a body portion where the passageway extends from a first opening in the body portion, e.g., a bone, to a second opening in the body portion. A suture may be placed in or otherwise secured to a material, e.g., a tissue, prosthetic, surgical implant, etc., to be secured relative to the body portion and two ends of the suture extending away from the material may be positioned in the first opening and extend into the passageway. The material may be secured relative to the body portion by securing the two ends of the suture in the passageway relative to the body portion near the second opening. For example, a rotator cuff tendon may be secured to a humerus by a suture that is placed in the tendon and has two ends that extend through a passageway in the humerus having one opening near the rotator cuff and a second opening positioned away from the rotator cuff, such as at a lateral side of the humerus. The two ends of the suture may be positioned in the passageway and secured at or near the second opening at the lateral side of the humerus. In one embodiment, a suture fixation device may be positioned near the second opening to help secure the two suture ends.

In one aspect of the invention, a suture fixation device used to help secure a suture relative to a passageway in bone may be arranged so as to secure the suture relative to the bone at an opening into the bone by having a portion of the suture fixation device positioned outside of and adjacent the opening in contact with portions of cortical bone. By securing the suture (and potentially a tissue or other material engaged with the suture) relative to the bone by contact of the suture fixation device with cortical bone, the suture may be more securely fixed as compared to devices that engage with softer cancellous bone.

In another aspect of the invention, a suture fixation device may include a body having an inner end and an outer end and a pathway extending between the inner and outer ends. The inner end may be arranged to be positioned in a hole in a body portion, such as bone. The body may include a restriction in the pathway that relatively freely permits movement of a knotless suture through the pathway in a first direction and inhibits movement of the knotless suture through the pathway in a second direction opposite the first direction.

Various aspects of the invention may be used in an open surgical procedure or in a closed procedure, such as an arthroscopic procedure. Also, various aspects of the invention may be used in any suitable surgical or other procedure involving any suitable body portions, such as bone, muscle, skin, vascular structures, digestive structures or other tissue, implants, mesh, or other medical devices, etc.

Figure 3:
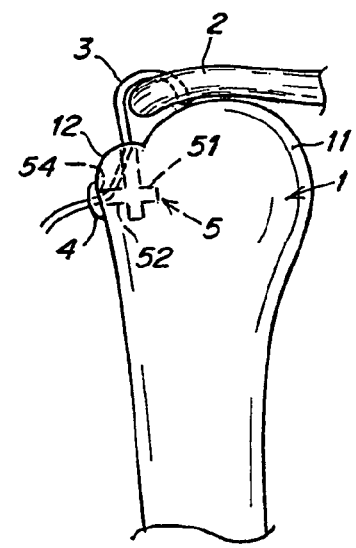
FIG. 3 is a schematic diagram of a tissue repair arrangement in accordance with an aspect of the invention.
Figure 4A:
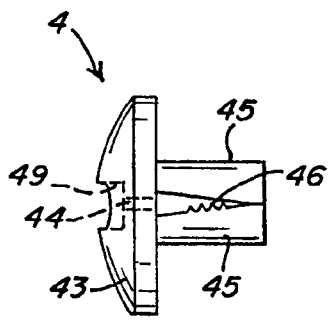
FIGS. 4A-B and 5A-B show side and rear views, respectively, of illustrative embodiments of suture fixation devices in accordance with the invention.
Figure 4B:
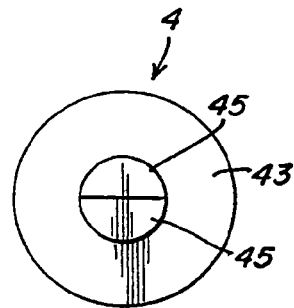
Figure 5A:
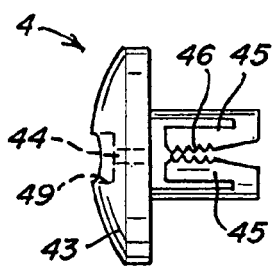
Figure 5B:
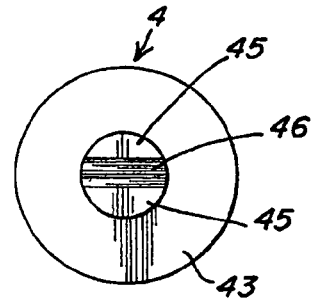

FIG. 3 shows a schematic diagram of a surgical repair in accordance with aspects of the invention. As discussed above, although aspects of the invention are described with reference to a rotator cuff repair for ease of reference and understanding, aspects of the invention may be used in any surgical or other procedure, and may involve any suitable body portions, such as bone, muscle, other tissue or combinations thereof, medical implants or other devices, etc. Thus, aspects of the invention are in no way limited to the specific embodiments and examples described herein.

In this illustrative embodiment, a rotator cuff tendon 2 is secured by a suture 3 relative to a humerus 1. The suture 3 is placed in the tendon 2, for example, using a mattress stitch or other arrangement, and is passed through a passageway 5 formed through the humerus 1. In this embodiment, the passageway 5 is formed by first and second intersecting holes. A first hole 51 is formed vertically as shown in FIG. 3 from a first opening at or near a margin between the articulating surface 11 and the greater tuberosity 12 of the humerus 1. The second hole 52 is formed horizontally as shown in FIG. 3 from a lateral position on the humerus 1. The suture 3 is secured at the second opening 54 of the second hole using a suture fixation device 4 that is positioned adjacent the second opening 54. Although in this embodiment the first and second holes 51 and 52 are arranged at approximately right angles, the first and second holes may be arranged at any suitable angle and may be colinear (i.e., at a 180 degree angle relative to each other). Alternately, the passageway 5 may be formed by a single, straight hole.

A wire, other material or the suture 3 may be manipulated in the passageway 5 so as to cut through or crush the relatively soft cancellous bone of the humerus in the passageway 5 so that the suture follows a relatively straight path between the first and second openings into the first and second holes 51 and 52. The relatively straight pathway may be formed by a "flossing" operation, such as by using a wire that is passed through the passageway 5 and is manipulated, e.g., tensioned and reciprocally drawn between the first and second openings, so as to cut through or crush the cancellous bone, thereby forming a relatively straight path for the suture 3.

In one aspect of the invention, the suture fixation device 4 is arranged so as to contact cortical bone near an opening of a passageway in which the suture is positioned. Such an arrangement may provide for more secure fixation of the suture as compared to suture fixation devices that engage mainly or exclusively with cancellous bone, which is generally "softer" than cortical bone. For example, the suture fixation device 4 may include a flange portion that contacts the bone portion around the hole with which the suture fixation device 4 is associated. Although embodiments of a suture fixation device herein are described as cooperating with a passageway in bone, it should be understood that the passageway may be formed in any suitable body portion in accordance with various aspects of the invention.

Figure 6:
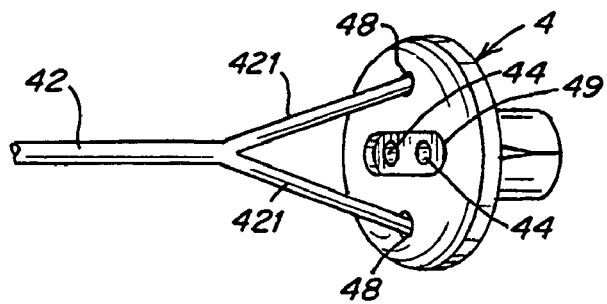
FIG. 6 shows a suture fixation device engagement tool in engagement with a suture fixation device in accordance with the invention.

FIGS. 4A-B and 5A-B show side and rear views of illustrative embodiments of suture fixation devices 4 in accordance with the invention. FIG. 6 shows a perspective view of an outer end of the suture fixation devices 4. In these embodiments, the suture fixation devices 4 include a restriction in a pathway through the suture fixation device 4 so that suture or other material passing through the pathway is relatively freely moved in one direction through the pathway, but movement of the suture or other material in the other direction in the pathway is resisted. For example, movement of a suture though the suture fixation devices shown in FIGS. 4A and 5A in a direction to the left may be freely allowed, while movement of the suture toward the right may be resisted. In the embodiment of FIG. 3 above, the restriction may aid in maintaining tension on the suture 3, e.g., while a knot is formed in the suture 3. For example, the suture 3 may be pulled from the second hole 52 through the suture fixation device 4 until the rotator cuff or other material is appropriately tensioned. Thereafter, the suture 3 may be temporarily released, e.g., in preparation for forming a knot, but movement of the suture back through the suture fixation device 4 may be resisted so that tension is maintained on the rotator cuff or other material, which may remain in place until the suture knot is tied or the suture is otherwise secured. In some embodiments, the restriction in the suture fixation device 4 may provide for knotless fixation of the suture. Alternately, knotless fixation of the suture may be provided by other features, such as an interference pin, locking cap, etc.

In the FIG. 4 embodiment, the suture fixation device includes an outer end having a flange portion 43 that is sized and arranged to contact the cortical bone adjacent the opening in the passageway at which the suture fixation device 4 is positioned, e.g., the second opening 54. One or more pathways 44 may be formed through the suture fixation device 4, such as by a hole or holes formed through the flange 43 (see FIG. 6). Instead of having multiple holes, the pathway 44 may include a single slot arranged to receive one or more sutures. A recess 49 may be provided in the flange portion 43 to receive one or more knots, if formed with the suture(s) in the pathway 44. A pair of duck bill members 45 at an inner end of the suture fixation device 4 may extend rearwardly from the flange 43 and may be arranged as to be positionable in the second hole 52. A groove between the duck bill members 45 may extend across the inner end of the suture fixation device 4 so that the members 45 may move independently of each other. In this embodiment, the groove separating the duck bill structures 45 extends from the flange portion 43 to the innermost end of the device 4 so that the structures 45 are pivotable at a point near the flange portion 43. The duckbill members 45 may be resiliently biased toward each other so as to resist the passage of suture or other material through the pathway 44. One or both of the duck bill structures 45 may include serrations 46 or other features that may aid in engaging a suture or other material.

The FIG. 5 embodiment similarly includes a flange 43 and one or more pathways 44. Duck bill structures 45 are also provided. However, in this embodiment rather than being hinged at a point near respective connection points with the flange 43, the duck bill portions 45 are hinged at a point positioned away from the flange 43 toward the inner end. Providing the effective hinge points for the duck bill structures 45 in this manner may provide improved engagement of the duck bill structures 45 with a suture or other material when the suture is urged to move from the outer end toward the inner end through the pathway 44. That is, if the suture is pulled to move toward the inner end, serrations 46 or other features may engage with the suture and increased force on the suture will cause an increased force urging the duck bill structures 45 to move toward each other and further squeeze the suture. The duck bill structures in the FIGS. 4 and 5 embodiments or other suitable suture engagement arrangements (such as interference pins, locking caps, internal locking hubs, etc.) may provide a knotless fixation for the suture. Alternatively, the structures may resist movement of the suture so as to aid the surgeon's ability to maintain tension on the suture while forming a knot.

Although this embodiment depicts the flange of the device resting on the outer cortical surface of the bone, the device may be positioned in a hole which has a counterbore, or countersink, in order to prevent any interference between the flange and other bone or tissues that may come in contact with the site either at rest or during movement. Thus, in one embodiment, the device may be arranged so the device does not extend above adjacent bone surfaces. Even in the case where the device is positioned in a counterbore or countersink feature, the device may contact cortical bone within the countersink or counterbore. Alternately, the device may only contact the outer, cortical surface of the bone, and not extend into a hole in the bone. The device may be held in place by virtue of its engagement with the suture.

Of course, it should be understood that suture fixation devices may be provided in any suitable form. For example, the duck bill portions 45 extending from the flange 43 in the FIGS. 4 and 5 embodiments may be sized to closely fit into a mating hole formed in bone. This close fit may help in maintaining the suture fixation devices 4 in a desired position in the bone. Alternately, the duck bill structures 45 may be formed so as to be tapered on their outer surfaces. Thus, when the suture fixation device 4 is inserted into a hole in the bone, the tapered surfaces of the duck bill structures 45 may contact the sides of the hole and urge the duck bill structures to move toward each other and lock the suture in place as the suture fixation device 4 is pressed into the hole. In another embodiment, a portion of the suture fixation device 4 that is inserted into a hole may have a screw thread, resilient arms or otherwise be arranged so as to engage the hole and help prevent the suture fixation device from falling from the hole, e.g., before the suture is secured in place. There are many variations of the mechanism form to retain the suture with respect to the device. Some of these forms may require a knot for final fixation. Other capturing mechanisms may provide sufficient locking of the suture such that a knot is not required. Theses are typically known as "knotless" devices. The devices 4 may be made of any suitable material or combination of materials, such as metal, plastic, composites or other. In one embodiment, the suture fixation devices may be made of a bioabsorbable material.

Figure 7:
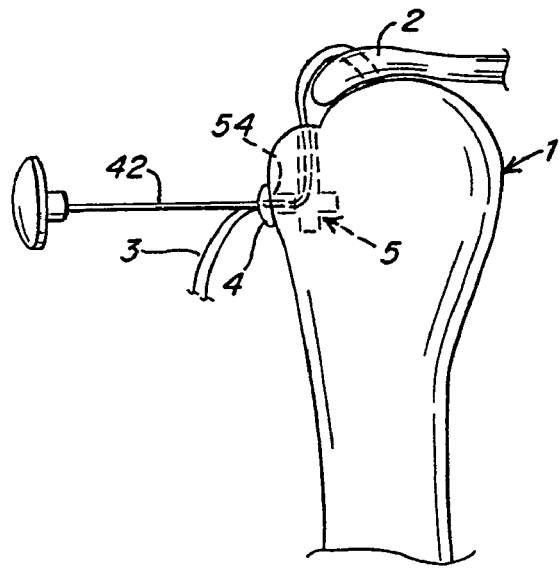
FIG. 7 shows the placement of a suture fixation device relative to the bone in accordance with the invention.

As shown in FIG. 6, the suture fixation devices 4 may be handled, e.g., passed through an arthroscopic cannula and set in place with respect to a body portion, using an applier that releasably engages with the suture fixation devices 4. For example, an applier 42 may have a pair of tines 421 that engage with recesses or other features on the suture fixation device 4 so as to removably engage with the suture fixation device 4. The tines 421 may be resilient so that the tines are squeezed together when engaged with the suture fixation device 4. Thus, an elastic force biasing the tine ends apart may help maintain engagement of the tines with the grooves 48 in the suture fixation device 4. Alternately, the tine ends may be force-fit into grooves 48 in the suture fixation device so that engagement is maintained based on friction. Of course, it will be understood that the applier 42 may engage with the suture fixation device 4 in any other suitable way, such as with a screw-in or snap mechanism. As shown in FIG. 7, the suture fixation device 4 may be positioned relative to the second opening 54 of the passageway 5 using the applier 42 which may be selectively disengaged from the suture fixation device when the suture fixation device 4 is positioned as desired.

Figure 8:
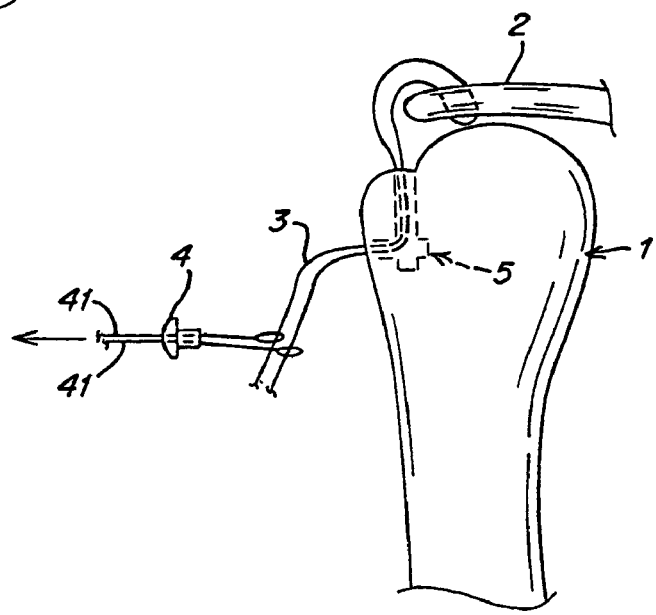
FIG. 8 shows the engagement of a suture with a suture fixation device in accordance with the invention.

As discussed above, the suture fixation devices 4 may have one or more pathways 44. As shown in FIG. 8, ends of suture 3 may be passed through respective holes in the suture fixation device 4 using one or more feed members 41. The feed members 41 may have an elongated shape, e.g., a wire or needle shape, that is passed through a respective hole in the suture fixation device 4. A loop at one end of the feed member 41 may receive an end of the suture 3 and thereafter the feed member 41 may be pulled through a respective hole in the suture fixation device 4 so as to pull the suture 3 through the hole. Of course, it should be understood that the suture 3 may be fed through the suture fixation device 4 in any other suitable way. For example, the feed member 41 may include one or more flat plates or strips, e.g., made of metal or plastic, with a hole or recess to accept suture. The flat configuration may allow for easy passage through the restriction portion of the device. Although some resistance may be encountered when feeding the portion of the feed member 41 that engages the suture through the restriction, permanent damage or other compromise of the resistive properties of the restriction may be avoided. When performing this technique, arthroscopically, the suture 3 may be fed through the suture fixation device 4 either inside or outside of the body cavity.

With the suture fixation device 4 in place relative to the second opening 54, the suture 3 may be tensioned so as to appropriately position the rotator cuff 2 relative to the humerus 1. At this point, the suture 3 may be fixed relative to the suture fixation device 4, such as by tying a knot with the suture ends. Thus, the suture fixation device 4 may provide not only a structure to support the suture knot, but also may spread the force of the suture 3 to portions of the relatively hard cortical bone surrounding or otherwise adjacent to the second opening 54. By having the suture fixation device 4 engage with this cortical bone, the suture fixation device 4 may provide a relatively stable and secure fixation point for the suture 3. The suture fixation device 4 may also incorporate a mechanism for knotless fixation of the suture, such as an interference pin, a locking passageway, a locking cap, etc.

Although in the illustrative embodiment described above both ends of the suture 3 are passed through the passageway 5 and secured at or near the second opening 54 of the passageway 5, the suture 3 may be secured in other ways, such as by passing one end of the suture 3 through the passageway 5 and passing another end of the suture 3 around the outside of the bone (e.g., over a portion of the greater tuberosity) where it is secured to the other suture end. In another embodiment, two passageways 5 may be formed through the bone and one end of the suture 3 may be passed through one passageway and the other end of the suture 3 may be passed through the other passageway. The suture ends may then be secured to each other at or near respective second openings of the passageways 5 on the lateral side of the humerus 1. In yet another embodiment, two or more first holes 51 may be formed so as to intersect with one or more second holes 52. Suture 3 may be passed through the two or more first holes 51 and be secured at the second opening 54 of the one or more second holes 52. Such an arrangement may allow for the use of a single second hole 52 and suture fixation device 4 to secure the rotator cuff at two or more points on the humeral head using two or more sutures that pass through different first holes 51. Other suture fixation techniques may be used as desired. However, in all of these techniques, a suture fixation device in accordance with aspects of the invention may be used.

Below, various other aspects of the invention that relate to forming a passageway in a body portion, providing suture in a passageway, etc. are described. These aspects may or may not be used with aspects of the invention that relate to a suture fixation device and its use. The aspects of the invention are described below with reference to a surgical procedure regarding the repair of a rotator cuff. However, it should be understood that aspects of the invention may be used in any suitable procedure.

When deciding where to locate the first hole 51 for a passageway 5 in a rotator cuff repair, a surgeon often will wish to first determine the final position for the tissue relative to the bone. To do so, the surgeon may wish to place a suture in the tendon 2 and tension the suture 3 (and thus the tendon 2) so that a desired position for the first hole 51 may be determined, e.g., based on the position of the tendon 2 relative to the bone when under tension.

Figure 9:
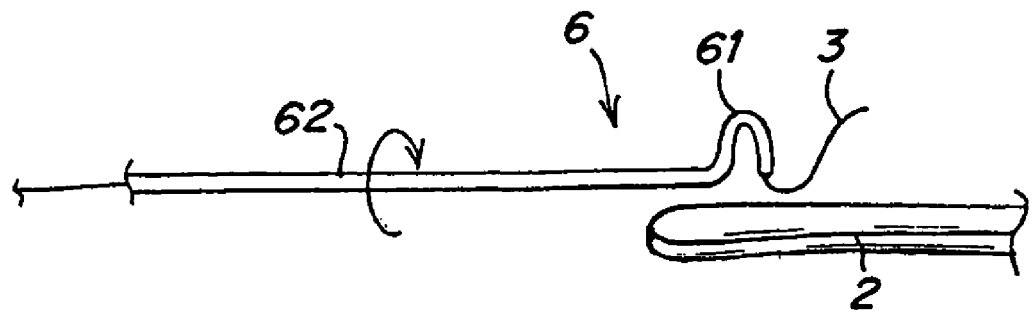
FIGS. 9-11 show the use of a needle for placing a suture in a tissue in accordance with the invention.
Figure 10:
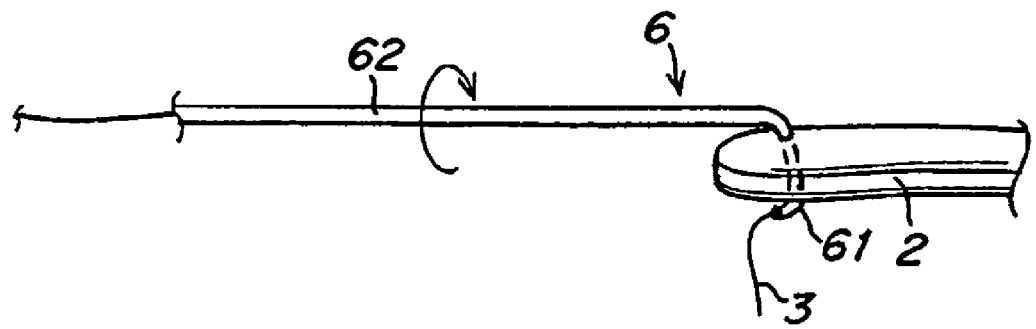
Figure 11:
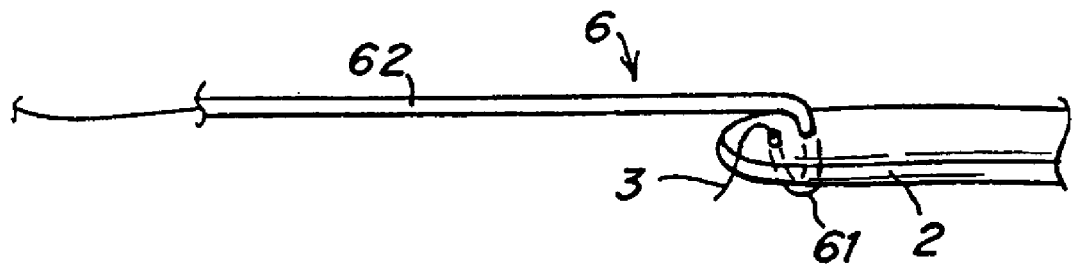

In various aspects of the invention, a suture may be placed in the tendon or other tissue 2 using any suitable technique, such as a standard suturing needle and forceps, specialized suturing devices, and so on. However, in one aspect of the invention, use of a needle having a hook-shaped or curved end portion may be preferred. FIGS. 9-11 show an embodiment of a needle 6 having a hook-shaped tissue penetrating portion 61 at a distal end in accordance with the invention. In the illustrated embodiment, the tissue penetrating portion 61 of the needle 6 has a semi-circular shape and is arranged at an angle, such as 90 degrees to a longitudinal axis of a straight portion 62 of the needle 6. The needle 6 may be formed as a hollow tube so that the suture 3 may pass through the needle 6. Suture may be loaded in the hollow portion of the needle 6 before the surgical procedure is begun, e.g., at the time of manufacture of the needle, or at any suitable time, such as during the surgical procedure. In some cases, the suture may be fed into the hollow portion of the needle 6 before the tissue penetrating portion 61 is formed, e.g., by bending a tube to form a curved end shape.

The arrangement of the needle 6 may allow placement of a mattress stitch in the tissue 2 by rotating the needle as shown in FIGS. 9-11 so that a tip of the tissue penetrating portion 61 passes through a top side of the tissue 2 and exits from a bottom side of the tissue 2 as shown in FIG. 10, and then passes upwardly through the tissue 2 to reemerge at a top side of the tissue 2 as shown in FIG. 11. At this point, the suture 3 extending from the tip of the tissue penetrating portion 61 may be grasped, such as by forceps or other gripping device, and the needle 6 may be rotated in reverse so as to again position the needle 6 as shown in FIG. 9, thereby leaving the suture 3 positioned in the tissue 2 to form a mattress stitch. During the passage of the suture, the tissue or other material may be held in place, or may be manipulated, by a grasper or other device inserted into the lumen of the cannula. The tissue or other material may also be held in place, or manipulated, by another device, such as a grasper or clamp positioned external to the cannula.

The tissue penetrating portion 61 of the needle 6 may have any suitable shape and may be arranged in a plane that is transverse at any angle to an axis of rotation of the tissue penetrating portion 61 when placing a suture in tissue. That is, although in the illustrated embodiment the tissue penetrating portion 61 has a semi-circular form that lies in a plane at 90 degrees to the rotation axis of the tissue penetrating portion 61 when placing a suture, the tissue penetrating portion 61 need not have a semi-circular form and may lie at any desired angle to the rotation axis. For example, the tissue penetrating portion 61 may be arranged so as to place an inclined mattress stitch in a tissue 2. Further, the needle 6 need not be used only to form a mattress stitch, but rather may be used to form any other suitable stitch type. Also, it is not necessary that the tissue penetrating portion 61 of the needle 6 lie in a single plane. Instead, the tissue penetrating portion 61 may not lie in a single plane, e.g., may have a corkscrew-type or partially helical configuration.

In one aspect of the invention, all or portions of a tissue repair procedure may be performed arthroscopically. In this case, and as is known in the art, one or more cannulas may be provided in one or more portals formed in the patient so as to provide access to the operative site. In one aspect of the invention, a needle used to place a suture in a tissue, such as the needle 6 shown in FIG. 9, may be used in an arthroscopic procedure. For example, the needle 6 may be secured to a cannula so that the needle may be operated by manipulation of the cannula.

Figure 12:
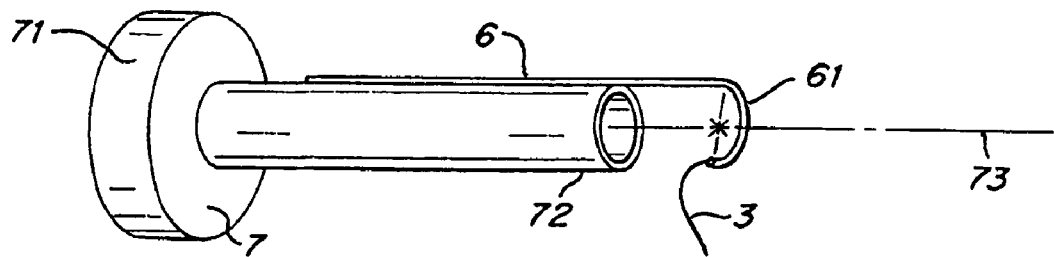
FIG. 12 shows a needle in engagement with a cannula in accordance with an aspect of the invention.

FIG. 12 shows an illustrative embodiment of a needle 6 that is secured to a cannula 7. The cannula 7 may have any suitable features found in cannulas used for closed or minimally-invasive surgical techniques, such as one or more valves to resist fluid flow through the cannula 7, an opening through which to introduce a fluid pressure or vacuum, spiral threads or other features on the cannula to aid in placement of the cannula in a portal and/or to help prevent inadvertent removal of the cannula from the portal, and so on. The cannula 7 may be arranged for any type of procedure, such as arthroscopic procedures.

The needle 6 may be secured to the cannula 7 in any suitable way. For example, the needle 6 may be molded into the body of the cannula 7, inserted into the wall of the cannula, may be secured by adhesive, welding, clamps, fasteners, interlocking channels, open channels, or any other suitable device. A proximal end of the needle 6 may terminate at any suitable point, such as midway between a proximal end 71 and a distal end 72 of the cannula 7 as shown, or, more preferably at a position proximal to the proximal end 71. By having the proximal end of the needle 6 positioned proximally of the cannula 7, a user may be better able to access the suture 3 entering the proximal end of the needle 6. The needle 6 may also be axially movable relative to the cannula, e.g., so that the tissue penetrating portion 61 may be moved axially so as to extend away from or toward the distal end 72 of the cannula 7. In addition, although the needle 6 is shown as positioned on an outer surface of the cannula 7, the needle 6, or at least a portion thereof, may be molded into the cannula 7, positioned within the cannula lumen, positioned within the cannula wall, may be arranged within a groove on the outer surface of the cannula, and so on. Although the needle 6 is shown as arranged in an approximately straight fashion along the length of the cannula 7, the needle 6 may be bent, curved or arranged in any suitable way, such as following a spiral path around an outer surface of the cannula 7.

In one illustrative embodiment, a semicircular-shaped tissue penetrating portion 61 of the needle 6 may be arranged relative to the cannula 7 so that a centerpoint of the semicircle lies on a central longitudinal axis 73 of the cannula lumen. Thus, when the cannula 7 is rotated about the central longitudinal axis 73, the tissue penetrating portion 61 may travel in a circular path about the axis 73. However, it should be understood that the tissue penetrating portion 61 may be arranged in any suitable way relative to the axis 73. Further, a plane in which the tissue penetrating portion 61 lies (if present) may be arranged at any angle transverse to the axis 73, and thus need not be arranged at an angle of 90 degrees to the axis 73, as shown in FIG. 12.

In one aspect of the invention, the needle 6 may be removeably engaged with the cannula 7 so that the needle 6 can be selectively engaged or disengaged with the cannula 7. For example, a cannula 7 may be positioned in a portal in use during a surgical procedure without an attached needle 6. At some point during the procedure, the surgeon may wish to attach a needle 6 to the cannula 7 and manipulate the cannula 7 so as to use the needle 6 to place a suture in a tissue. The needle 6 may be secured to the cannula while the cannula remains in place in the portal (e.g., by inserting the needle 6 into the cannula lumen), or the cannula may be removed from the portal, the needle attached, and the cannula and attached needle inserted into the portal.

Figure 13:
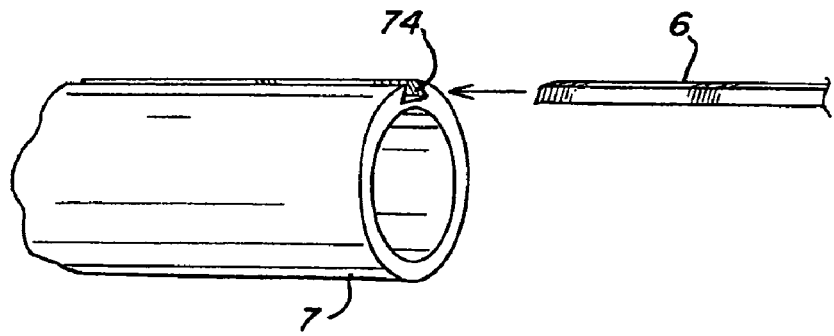
FIG. 13 shows an illustrative arrangement for engaging a needle with a cannula in one embodiment.

FIG. 13 shows one illustrative embodiment in which a needle 6 may be removably secured to a cannula 7. In this embodiment, the cannula 7 includes a dovetail-shaped groove 74 into which a correspondingly shaped portion of the needle 6 is inserted. The complementary locking arrangement used by the cannula 7 and the needle 6 need not necessarily be dovetail-shaped as shown in FIG. 13, but rather may have any suitable arrangement. Thus, the needle 6 may be selectively secured to the cannula 7 so that rotation or other manipulation of the cannula 7 can cause the needle to be manipulated so as to place a suture in a tissue. The complementary locking arrangement between the needle 6 and the cannula 7 may also allow for axial movement of the needle 6 relative to the cannula 7, e.g., so the tissue penetrating portion 61 can be moved relative to the distal end 72 of the cannula 7.

Figure 14:
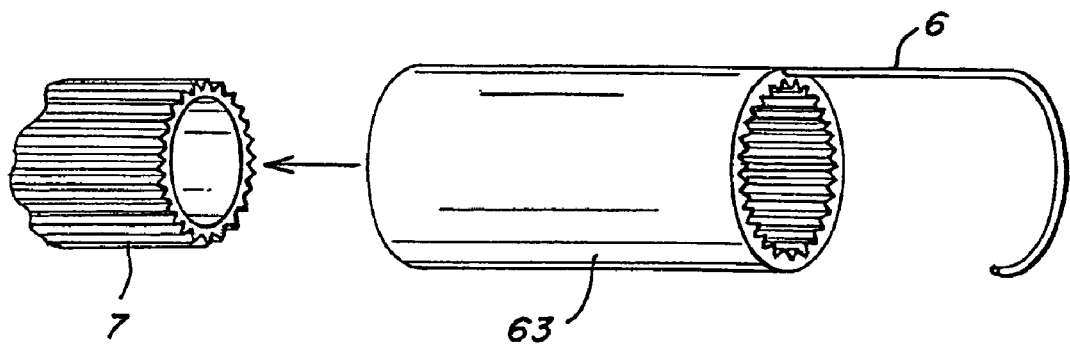
FIG. 14 shows an illustrative arrangement for engaging a sleeve and needle assembly with a cannula in accordance with another embodiment.

FIG. 14 shows an alternative embodiment in which a needle 6 is fixed to a sleeve member 63 that has one or more complementary locking features that mesh with or otherwise engage with complementary features on the cannula 7. In this embodiment, the complementary locking features have a tooth-like or gear-like form, but the complementary locking features may be arranged in any suitable way. Accordingly, in this embodiment, the needle 6 may be secured to the cannula 7 by sliding the sleeve 63 over the distal end 72 of the cannula 7. It will be understood that rather than having a sleeve 63 that fits over the cannula 7, the sleeve 63 may fit within the internal lumen of the cannula 7, or within a slot in the cannula 7, if desired.

Once a suture is placed in the tissue, such as a rotator cuff tendon, the tissue may be tensioned to determine a location for the opening of the first hole 51 to be formed in the bone. When performing a rotator cuff repair, typically, a first hole 51 of the passageway 5 will be formed vertically from a superolateral position so that the first hole 51 is generally aligned along the length of the humerus 1 and extends into the bone from an opening formed at the margin between the articulating surface 11 and the greater tuberosity 12. This first hole 51 may be formed using a perforator, such as a drill, awl, punch or other suitable device. As with other procedures performed, the first hole 51 may be formed using an arthroscopic portal at a superolateral position, or may be formed in an open surgical procedure.

Figure 15:
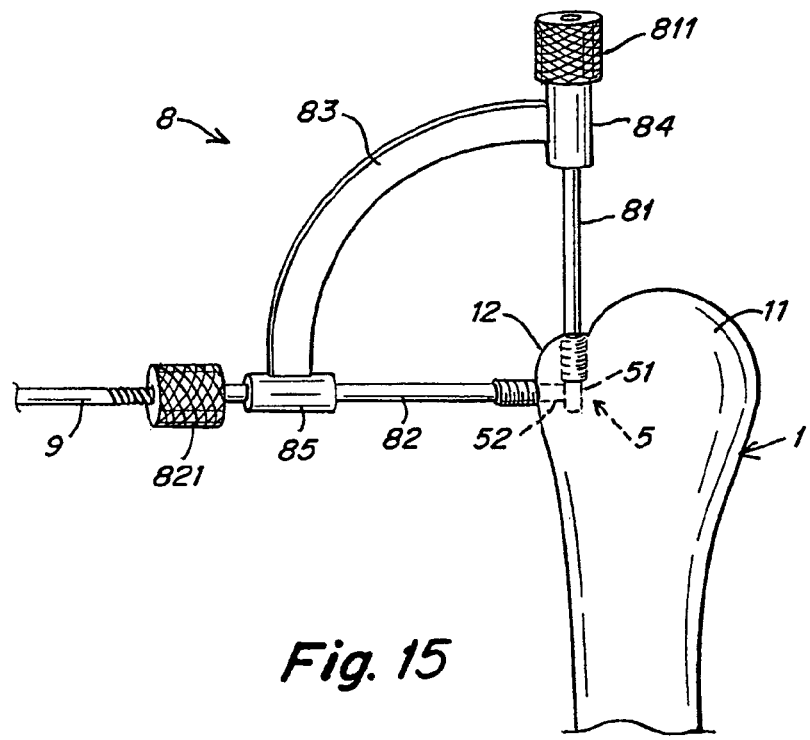
FIG. 15 shows a guide apparatus used in forming a passageway in accordance with the invention.

In accordance with an aspect of the invention, a guide apparatus may be used to form the first and/or second holes of the passageway (e.g., used to locate a starting point or opening for the first and second holes or used to orient a bone perforator when making the holes), or may be used to help feed a suture or suture-like material through the passageway. For example, a first guide member 81 may be secured relative to the first hole 51, as shown in FIG. 15. The first guide member 81 may be part of a guide apparatus 8 used to guide the formation of holes used to form a passageway in bone and/or to pass a suture or other material through the passageway. In the illustrated embodiment, the first hole 51 has been formed in a vertical direction along the length of the humerus 1, e.g., by drilling the hole in a freehand manner. The first guide member 81 may include a feature to help secure the first guide member 81 relative to the first hole 51, such as a threaded distal end that allows the first guide member 81 to be screwed into the bone to a desired depth in the first hole 51. It should be understood, however, that the distal end of the first guide member 81 need not be threaded, but instead may unthreaded and inserted into the first hole 51. Alternately, the distal end of the first guide member 81 may be positioned outside of, but adjacent to, the first hole 51 so that a lumen in the first guide member 81 aligns with the first hole 51. The first hole 51 may be formed so as to be deeper than thought to be needed, e.g., 0.5 cm deeper than a hole depth believed to be required. This overdrilling of the first hole 51 may allow for more flexibility in positioning the first guide member 81 to a desired depth in the bone.

Prior to securing the first guide member 81 relative to the first hole 51, the first guide member 81 may be arranged with respect to a reference structure 83. The reference structure 83 may be used to position first and second guide members 81 and 82 relative to each other in the passageway 5, as is discussed in more detail below. In this illustrative embodiment, the reference structure 83 is arranged so that the first and second guide members 81 and 82 are positioned at a 90 degree angle relative to each other when engaged with the reference structure 83. However, the reference structure 83 may be arranged in any suitable way so as to orient the first and second guide members 81 and 82 at any desired angle relative to each other, including arranging the first and second guide members 81 and 82 in a co-linear fashion. Further, the reference structure 83 may be made so as to be adjustable, thereby allowing the orientation of the first and second guide members 81 and 82 to be changed. For example, the arc-shaped connecting portion of the reference structure 83 may be made so as to be adjustable in length, e.g., having one arc-shaped portion sliding relative to another arc-shaped portion to allow adjustment of the length of the connecting portion. Alternately, or in addition, engagement portions 84 and 85 of the reference structure 83 that engage with the first and second guide members 81 and 82 may be adjustable in orientation relative to the arc-shaped connecting portion. In short, the reference structure 83 may be arranged in any suitable way so as to allow adjustment in the orientation of the guide members 81 and 82.

In this illustrative embodiment, the engagement portions 84 and 85 include sleeves that receive at least a portion of the guide members 81 and 82, e.g., the guide members 81 and 82 may be received in bores in the sleeves. The sleeves may be arranged so that the guide members 81 and 82 are movable linearly along their longitudinal axes and rotationally about their longitudinal axes relative to the engagement portions 84 and 85, but otherwise may be relatively restricted in their range of movement. When a stop on the first guide member 81, such as a knob 811 on the proximal end of the guide member 81, contacts an engagement surface on the reference structure, such as a portion of the engagement portion 84, the second guide member 82 may be positioned by the reference structure 83 so that its longitudinal axis passes a point adjacent the extreme distal end of the first guide member 81. Thus, the second guide member 82 may be used to guide the use of a perforator 9 (such as a drill, punch, awl or other bone perforating device) so that the perforator 9 forms a second hole 52 that intersects with the first hole 51 at a location adjacent the distal end of the first guide member 81. As discussed above, the guide member 82 may guide the movement of the perforator 9, e.g., guide the movement of a drill or punch inserted into a lumen of the guide member 82 as shown, or may guide a starting location for forming the second hole, e.g., be used to mark or otherwise determine a starting location for the perforator 9, but otherwise not interact with the perforator 9.

Alternately, the engagement portion 85 may itself function as a perforator guide with the second guide member 82 being withdrawn from the engagement portion 85. Although in this illustrative embodiment the engagement portions 84 and 85 are shown as relatively short cylindrical sleeves, the engagement portions 84 and 85 may be arranged in any suitable way, e.g., may be elongated so as to more closely approach the humerus 1 and provide improved guidance for a perforator 9 and/or the first and second guide members 81 and 82. Further, the first guide member 81 may be arranged so that is rotationally movable about its longitudinal axis relative to the reference structure 83, but is otherwise held by the engagement portion 84 so that the first guide member 81 is not movable axially. This may aid is appropriately positioning the first guide member 81 and reference structure 83 when forming the second hole 52.

Figure 16:
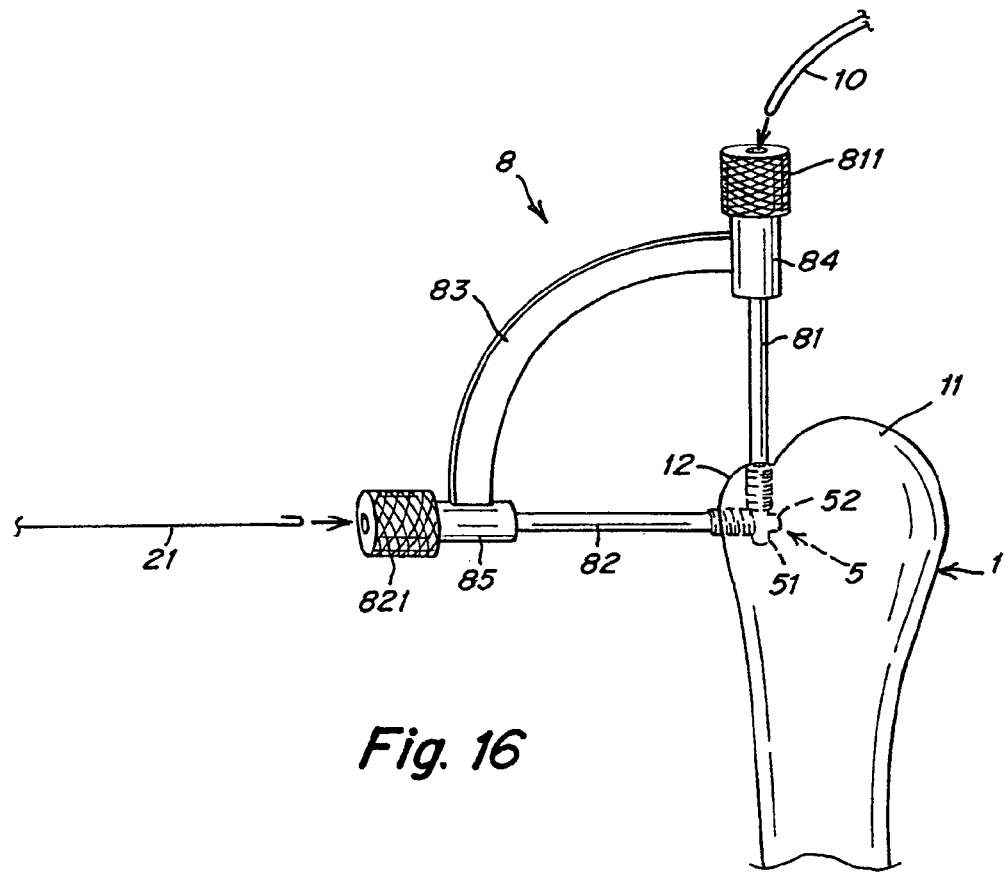
FIG. 16 shows the use of a guide apparatus for passing a suture or other element through a transosseous passageway in accordance with the invention.

Upon formation of the second hole 52, the second guide member 82 may be screwed into the second hole 52 until a stop on the second guide member 82, such as a knob 821 at a proximal end of the guide member 82, contacts an engagement surface on the engagement portion 85, such as a portion of the sleeve. In this configuration shown in FIG. 16 (stops on the first and second guide members 81 and 82 engaged with respective engagement surfaces on the reference structure 83), the extreme distal ends of the first and second guide members 81 and 82 may be adjacent to each other in the passageway 5 formed by the first and second holes 51 and 52. Accordingly, a surgeon may be assured that if the first and second guide members 81 and 82 are positioned within the bone and stops on the guide members 81 and 82 are respectively in contact with appropriate engagement surfaces on the guide apparatus 8, the extreme distal ends of the guide members 81 and 82 will be positioned adjacent each other. Thus, the surgeon may be assured that a wire 10 or other element may be fed into one of the guide members and retrieved from the other of the guide members, e.g., using a retriever 21 having a hook at a distal end. Such an arrangement may be advantageous when using the guide apparatus 8 in an arthroscopic procedure where the operative site may not be easily visualized.

Although in the above embodiment, stops on the first and second guide members 81 and 82 contact corresponding engagement surfaces on the engagement portions 84 and 85, the guide members 81 and 82 may be positioned relative to the reference structure 83 in any suitable way. For example, the guide members 81 and 82 may have indicator marks on them that may be aligned with a portion of the engagement portions 84 and 85, respectively. The alignment of certain indicator marks on the guide members 81 and 82 may be used to indicate, for example, that the distal ends of the guide members 81 and 82 are adjacent each other. Those of skill in the art will understand that the position of the guide members 81 and 82 relative to the reference structure 83 and relative to each other may be determined in other ways.

In this illustrative embodiment, the first guide member 81 is shown as having a smaller diameter (at least at the distal end) than the second guide member 82. This may allow the guide apparatus 8 to be used with an arrangement where the first hole 51 is smaller than the second hole 52. A relatively small first hole 51 may allow for more rapid healing and/or provide additional space for other holes in the margin, if needed. However, it should be understood that the guide apparatus 8 and/or the holes that form the passageway 5 may be made in any suitable way, e.g., the first and second holes 51 and 52 may have the same diameter or the first hole 51 may have a larger diameter than the second hole 52.

Although in this illustrative embodiment, the guide apparatus 8 is used to guide the formation of the second hole 52, the guide apparatus 8 need not necessarily be used to guide the formation of the second hole 52. That is, the guide apparatus 8 may be used only to help feed the wire 10, suture or other material through a passageway that is pre-formed in the bone or other body portion. In addition, the first and second guide members 81 and 82 may be arranged so that the members 81 and 82 can be secured in a body portion without requiring holes to be predrilled or otherwise formed. Thus, in one embodiment, the first and second guide members 81 and 82 may be arranged like an awl or other device capable of forming a hole in a body portion, e.g., capable of being forced into bone, forming the passageway 5 by their entry and/or providing a means to help feed a wire, suture or other material through the passageway 5.

Figure 17:
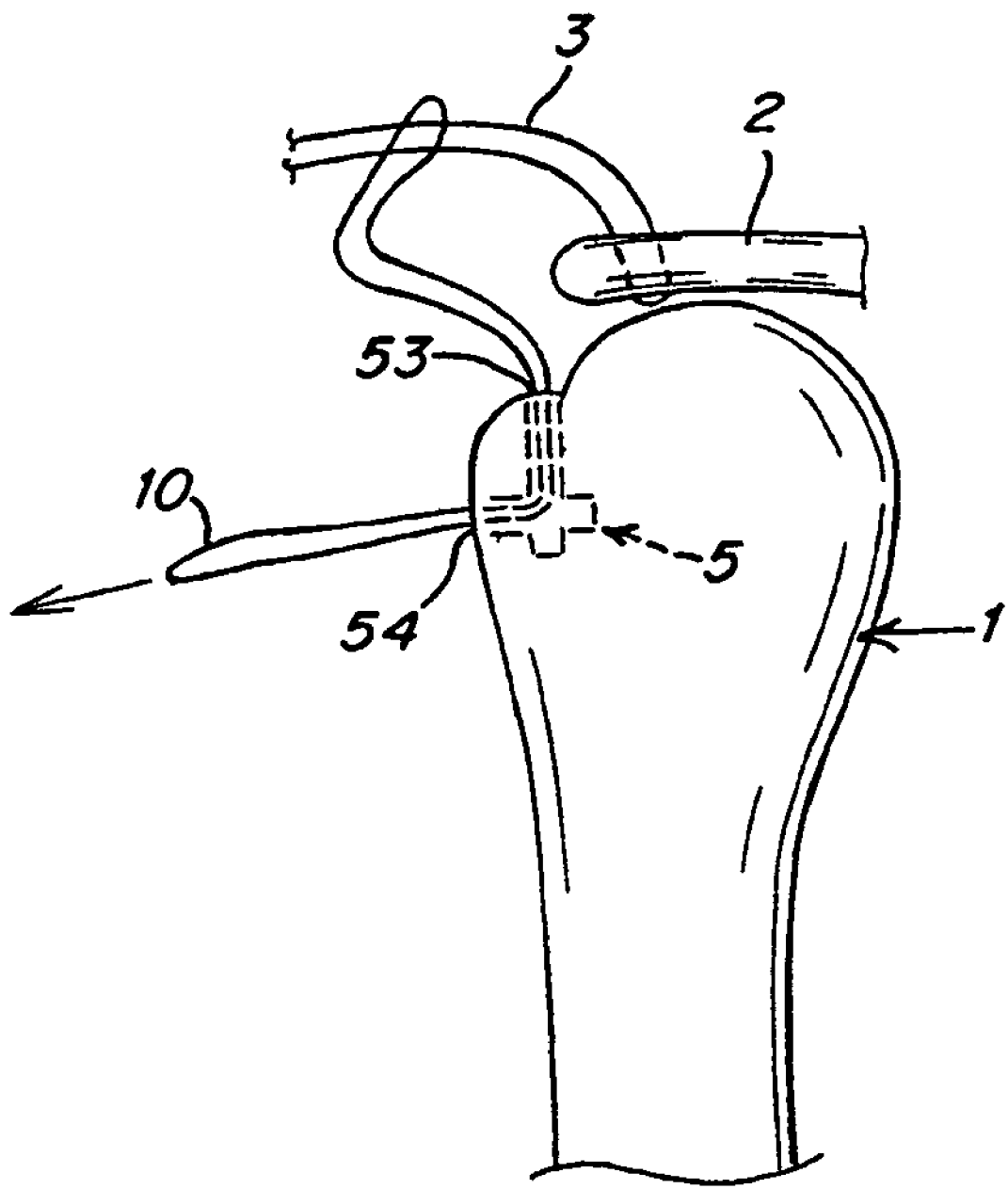
FIG. 17 shows a technique for passing a suture placed in a tissue through a passageway.

Once the wire 10, suture or other material has been passed through the passageway 5, as shown in FIG. 17, the wire 10 may be used to pull the suture 3 through the passageway 5. Prior to being used to pull the suture 3 through the passageway 5, the wire 10 or other material may be used to create a relatively straight pathway for the suture 3 once the suture 3 is tensioned and fixed in place. For example, the wire 10 may be tensioned between the first and second openings 53 and 54 of the first and second holes 51 and 52 or otherwise manipulated so as to cut or crush the body portion, e.g., bone, between the first and second openings 53 and 54. Such manipulation of the wire 10 may perform a kind of "flossing" effect in the bone, allowing the suture 3 to follow a more straight pathway through the passageway 5, reducing the length of suture 3 needed between the rotator cuff 2 and a point of fixation of the suture 3, e.g., near the second opening 54. The wire 10 may have barbs or other saw-like features to aid in cutting bone and forming the pathway. Reducing the length of suture 3 in the passageway 5 may improve the suture's ability to maintain appropriate tension on the rotator cuff 2, e.g., by reducing the amount of stretch of the suture when under tension.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method for performing a surgical repair, comprising:
   forming a passageway in bone by forming a first hole extending from a first opening into the bone and forming a second hole extending from a second opening into the bone such that the first and second holes intersect each other, the first opening being located near a soft tissue or implant material to be secured relative to the bone and the second opening being located remotely from the soft tissue or implant material;
   providing a suture in the passageway, without passing a suture fixation device attached to the suture through the passageway from the first hole to the second hole, so that the suture extends from within the bone toward the second opening;
   securing a portion of the suture located near the first opening to the soft tissue or implant material;
   providing a suture fixation device having an inner end, an outer end, and a non-tortuous pathway extending between the inner end and the outer end, the suture fixation device including restriction in the non-tortuous pathway that permits movement of a knotless suture portion through the pathway in a first direction and resists movement of the knotless suture portion in a second direction opposite the first direction;
   providing the suture in the pathway of the suture fixation device so as to provide a proximal portion of the suture extending from the outer end of the suture fixation device;
   pulling the proximal portion of the suture to move a knotless portion of the suture in the first direction relative to the restriction and to apply tension to the portion of the suture near the first opening to secure the soft tissue or implant material relative to the bone near the first opening; and
   releasing the proximal portion of the suture such that the knotless portion of the suture is held by the restriction to resist movement of the knotless portion of the suture in the second direction and to maintain tension on the suture and the soft tissue or implant material at the first opening, the suture fixation device having a portion positioned outside of the second opening and in contact with portions of cortical bone outside of and adjacent to the second opening.

2. The method of claim 1, wherein the step of forming a passageway includes forming a passageway through bone of a humerus, the passageway extending from the first opening at the margin of the humerus to the second opening at a lateral position on the humerus; and
   the suture fixation device is positioned in contact with bone outside of and adjacent the second opening at the lateral position.

3. The method of claim 2, wherein the suture fixation device has a flange portion that extends around the second opening at the lateral position.

4. The method of claim 1, wherein the suture fixation device includes a portion that extends into the second opening.

5. The method of claim 1, wherein the restriction includes portions that are biased toward each other to engage with suture in the pathway so that the restriction relatively freely permits movement of a suture through the passageway in the first direction out of the second opening and inhibits movement of the suture through the passageway in the second direction opposite the first direction.

6. The method of claim 1, wherein the
   suture fixation device is entirely positioned outside of the second opening.

7. The method of claim 6, wherein the fixation device is held in place adjacent the second opening by virtue of engagement of the fixation device with the suture.

8. The method of claim 7, wherein the step of providing a suture includes:
   providing the suture through the first opening and into the passageway so the suture extends through the passageway to the second opening.

9. The method of claim 1, wherein the step of providing the suture in the passageway comprises:
   providing a first end of a suture into the passageway so as to extend toward the second opening; and
   extending a second end of the suture to the suture fixation device without passing the second end of the suture through the passageway.

10. The method of claim 1, wherein the step of providing the suture into the passageway comprises:
    providing two ends of the suture into the passageway so the two ends extend to the second opening.

11. The method of claim 1, wherein:
    securing a portion of the suture located near the first opening to the soft tissue or implant material comprises securing the suture to a rotator cuff to be secured to the exterior of the bone near the first opening, and wherein pulling the proximal portion of the suture at the second opening secures the rotator cuff to the bone near the first opening.

12. The method of claim 1, further comprising:
    securing a portion of suture positioned outside of the passageway to the suture fixation device.

13. The method of claim 1, wherein the restriction of the suture fixation device includes two movable portions that are biased toward each other.

14. The method of claim 13, wherein the two movable portions form a duckbill structure with opposed surfaces that are biased toward each other.

15. The method of claim 1, wherein the first and second holes intersect and are transverse to each other.

16. The method of claim 1, wherein the suture fixation device is made of a metal or plastic.

17. The method of claim 1, further comprising:
forming a knot using the suture at the outer end of the suture fixation device.

18. The method of claim 1, further comprising:
fixating the suture to the suture fixation device by engaging a pin or cap with the suture fixation device.

19. The method of claim 1, wherein engagement of the restriction with the suture provides the sole fixation of the suture to the suture fixation device.

20. The method of claim 1, wherein multiple sutures are provided in the pathway of the suture fixation device.

* * * * *